United States Patent
Nakamura et al.

(10) Patent No.: US 7,307,181 B2
(45) Date of Patent: Dec. 11, 2007

(54) PROCESS FOR PRODUCING A NITRILE COMPOUND

(75) Inventors: Kenichi Nakamura, Niigata (JP); Shuji Ebata, Niigata (JP); Fumio Tanaka, Niigata (JP); Takuji Shitara, Niigata (JP)

(73) Assignee: Mitsubishi Gas Chemical Company, Inc, Tokyo (JP)

( * ) Notice: Subject to any disclaimer, the term of this patent is extended or adjusted under 35 U.S.C. 154(b) by 653 days.

(21) Appl. No.: 10/865,824

(22) Filed: Jun. 14, 2004

(65) Prior Publication Data

US 2005/0014944 A1    Jan. 20, 2005

Related U.S. Application Data

(63) Continuation-in-part of application No. 10/310,908, filed on Dec. 6, 2002, now abandoned.

(30) Foreign Application Priority Data

Dec. 13, 2001  (JP) .............................. 2001-379794

(51) Int. Cl.
  *C07C 253/24* (2006.01)
(52) U.S. Cl. ...................................... 558/310; 558/327
(58) Field of Classification Search ................ 558/310, 558/327
  See application file for complete search history.

(56) References Cited

U.S. PATENT DOCUMENTS 3,462,476 A    8/1969  O'Donnell et al.

FOREIGN PATENT DOCUMENTS

EP    1 113 001    7/2001

OTHER PUBLICATIONS

Communication and European Search Report dated Jun. 29, 2004, for No. EP 04 01 1336.

*Primary Examiner*—Golam M. M. Shameem
*Assistant Examiner*—Ebenezer Sackey
(74) *Attorney, Agent, or Firm*—Antonelli, Terry, Stout & Kraus, LLP.

(57) ABSTRACT

In a process for producing a nitrile compound comprising introducing a carbon ring or heterocyclic compound having organic substituents, ammonia and the air into a reactor and reacting the introduced compounds in the presence of a catalyst, during the reaction, a residual gas obtained after the formed nitrile compound is separated from a reaction gas discharged from the reactor is recycled to the reactor in an amount of 10 to 60% by volume based on the amount of the fresh raw material gas supplied to the reactor and the ratio of the amount by mole of molecular oxygen to the amount by mole of the organic substituent in the carbon ring or heterocyclic compound having organic substituents supplied to the reactor ($O_2$/organic substituent) is kept within 1.5 to 7. The reaction is achieved under an advantageous condition and the nitrile compound can be produced industrially advantageously at a higher yield.

16 Claims, 1 Drawing Sheet

PROCESS FOR PRODUCING A NITRILE COMPOUND

This application is a Continuation-in-part application of application Ser. No. 10/310,908, filed Dec. 6, 2002 now abandoned, the contents of which (where not inconsistent with the present application) are incorporated herein by reference in their entirety.

BACKGROUND OF THE INVENTION

1. Field of the Invention

The present invention relates to a process for producing a carbon ring or heterocyclic nitrile compound by ammoxidation using a carbon ring or heterocyclic compound having organic substituents as the raw material.

2. Description of the Related Arts

Carbon ring nitrile compounds are useful as raw materials for synthetic resins and agricultural chemicals and as intermediate compounds for amines and isocyanates. Heterocyclic nitrile compounds are useful as intermediate compounds for drugs and additives for feed and food.

The process of reacting an organic compound such as a carbon ring or heterocyclic compound having an organic substituent or organic substituents (hereinafter, occasionally referred to as a compound having organic substituents) with ammonia and a gas containing oxygen is called ammoxidation and, in general, nitrile compounds are produced in accordance with a gas phase catalytic reaction.

It is known that catalysts containing vanadium, molybdenum or iron are used for the ammoxidation. For example, in Japanese Patent Application Laid-Open No. Heisei 11(1999)-209332, a process for ammoxidizing aromatic hydrocarbon and heterocyclic compounds having alkyl groups as substituents in the presence of a catalyst containing oxides of V, Cr, B and Mo is described. In Japanese Patent Application Laid-Open No. Heisei 9(1997)-71561, a process for producing dicyanobenzene by the ammoxidation of xylene in the presence of a catalyst containing oxides of Fe, Sb and V is described.

SUMMARY OF THE INVENTION

The conditions of the reaction in the ammoxidation such as the composition of the feed gas, the contact time and the temperature of the reaction are important factors deciding the yield and productivity of the nitrile compound and must be controlled rigorously. On the other hand, when the nitrile compound is produced by the ammoxidation, the air is industrially used as the oxygen source. When the air is used as the oxygen source, it can frequently occur that the composition of the feed gas and the contact time cannot be selected at the optimum values since the content of oxygen in the air is constant. Pure oxygen and nitrogen may be used for adjustment of the composition of the feed gas. However, additional apparatuses for producing pure oxygen and nitrogen are required for using these gases and cost of construction of the facility increases. Therefore, this method is not preferable.

The present invention has an object of providing a process which, in the process for producing a nitrile compound using a carbon ring or heterocyclic compound having organic substituents, ammonia and the air as the raw materials in accordance with the gas phase catalytic ammoxidation, can achieve the reaction under excellent conditions by adjusting the composition of the feed gas and the contact time without additional facilities and provide the nitrile compound industrially advantageously in a high yield.

As the result of intensive studies by the present inventors to achieve the above object, it was found that the above object could be achieved when the residual gas component which was obtained after the formed nitrile compound was separated from the reaction gas of the ammoxidation was recycled to the reactor in a specific amount and the ratio of the amount by mole of molecular oxygen to the amount by mole of the organic substituent in the carbon ring or heterocyclic compound supplied to the reactor was kept in a specific range. The present invention has been completed based on the knowledge.

The present invention provides a process for producing a nitrile compound which comprises introducing a carbon ring compound having organic substituents or a heterocyclic compound having organic substituents into a reactor in combination with ammonia and an air and ammoxidizing the introduced compound in a presence of a catalyst, wherein, during the reaction, a residual gas component which is obtained after the formed nitrile compound is separated from a reaction gas discharged from the reactor is recycled to the reactor in an amount in a range of 10 to 60% by volume based on an amount of a fresh raw material gas comprising the carbon ring compound having organic substituents or the heterocyclic compound having organic substituents, ammonia and the air which are freshly supplied to the reactor and a ratio of an amount by mole of molecular oxygen to an amount by mole of the organic substituent in the carbon ring compound having organic substituents or the heterocyclic compound having organic substituents supplied to the reactor ($O_2$/organic substituent) is kept in a range of 1.5 to 7.

BRIEF DESCRIPTION OF THE DRAWINGS

In FIG. 1, 1 means a reactor of ammoxidation, 2 means a column for collecting a nitrile and 3 means a column for washing with water.

DESCRIPTION OF THE PREFERRED EMBODIMENTS

Figure 1:
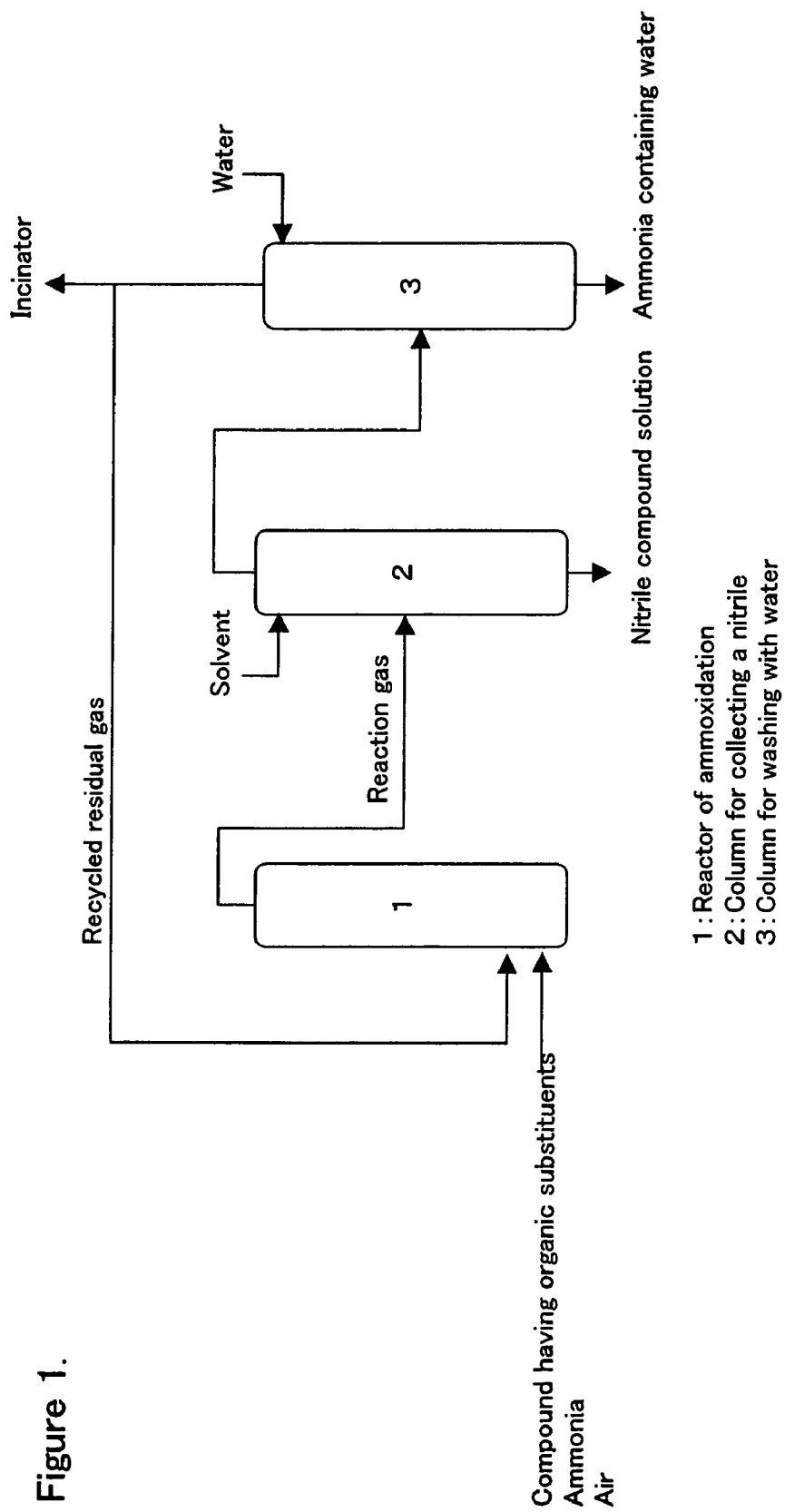
FIG. 1 shows a flow diagram exhibiting an embodiment of the process of the present invention. In this embodiment, the ammoxidation is conducted in accordance with the reaction using a fluidized bed. The reaction gas discharged from the reactor is brought into contact with a solvent and the reaction products are collected. The residual gas obtained after this step is brought into contact with water and ammonia is collected. The residual gas obtained after these steps is recycled to the reactor of ammoxidation.

The carbon ring compound having organic substituents which is used as the raw material in the present invention is a carbon ring compound having a carbon ring such as benzene ring, naphthalene ring, anthracene ring, cyclohexene ring, cyclohexane ring, dihydronaphthalene ring, tetraline ring and decaline ring and organic substituents such as methyl group, ethyl group, propyl group, formyl group, acetyl group, hydroxymethyl group and methoxycarbonyl group as the side chains on the carbon ring. The carbon ring compound may further have atoms and groups which do not take part in the ammoxidation such as a halogen atom, hydroxyl group, alkoxyl group, phenyl group, amino group and nitro group. Examples of the carbon ring compound having organic substituents include toluene, xylene, trimethylbenzene, ethylbenzene, methylnaphthalene, dimethylnaphthalene, methyltetraline, dimethyl-tetraline, chlorotoluene, dichlorotoluene, methylaniline, cresol and methylanisole.

The heterocyclic compound having organic substituents which is used as the raw material is a heterocyclic compound having a heterocyclic ring such as furan ring, pyrrol ring, indole ring, thiophene ring, pyrazole ring, imidazole ring, oxazole ring, pyran ring, pyridine ring, quinoline ring, isoquinoline ring, pyrroline ring, pyrrolidine ring, imidazoline ring, imidazolidine ring, piperidine ring and piperadine ring and organic substituents such as those described above as the side chains on the heterocyclic ring. The heterocyclic compound may further comprise as the side chains thereof atoms and groups which do not take part in the ammoxidation such as those described above for the carbon ring compound. Examples of the heterocyclic compound include furfural, 2-methylthiophene, 3-methylthiophene, 2-formylthiophene, 4-methyl-thiazole, methylpyridine, dimethylpyridine, trimethylpyridine, methyl-quinoline, methylpyrazine, dimethylpyrazine and methylpiperadine.

The compounds may be used singly or as a mixture of two or more. The present invention is advantageously applied to producing isophthalonitrile from meta-xylene having two methyl groups on the benzene ring among the above compounds.

In the present invention, the nitrile compound is produced by the ammoxidation in accordance with the gas phase catalytic ammoxidation. For the ammoxidation, for example, a fixed bed reactor, a moving bed reactor or a fluidized bed reactor may be used. The fluidized bed reactor is preferable from the standpoint of controlling the temperature of the reaction and cost of the apparatus. The catalyst used in the present invention is not particularly limited as long as the catalyst is suitable for the ammoxidation in accordance with the gas phase catalytic reaction. As the catalyst, for example, catalysts comprising an oxide of at least one element selected from vanadium, molybdenum and iron are preferable.

When the fluidized bed catalyst is used, the particle diameter of the catalyst is in the range of 10 to 300 μm. The average particle diameter is in the range of 30 to 200 μm and preferably in the range of 40 to 100 μm. The bulk density of the catalyst is in the range of 0.5 to 2 $g/cm^3$ and preferably in the range of 0.7 to 1.5 $g/cm^3$.

In the present invention, ammonia of the industrial grade can be used as ammonia. The amount of ammonia expressed as the ratio of the amount by mole of ammonia to the amount by mole of the organic substituent in the carbon ring or heterocyclic compound of the raw material ($NH_3$/organic substituent) is in the range of 1 to 10 and preferably in the range of 3 to 7. When the amount of ammonia is less than the above range, the yield of the nitrile compound decreases. When the amount of ammonia exceeds the above range, industrial disadvantages arise since the loss or the cost of recovery of unreacted ammonia increases. In the present invention, the residual gas obtained after the nitrile compound of the object compound is separated from the reaction gas discharged from the reactor is recycled to the reactor of ammoxidation. When ammonia is contained in the residual gas in an amount more than the negligible amount, the amount of fresh supply of ammonia may be suitably adjusted.

In the present invention, the air is used as the oxygen source. The amount of the air is adjusted in a manner such that the ratio of the amount by mole of oxygen to the amount by mole of the organic substituent in the carbon ring or heterocyclic compound of the raw material ($O_2$/organic substituent) is in the range of 1.5 to 7 and preferably in the range of 1.5 to 5. When the amount of the air is less than the above range, the yield of the nitrile compound decreases. When the amount of the air exceeds the above range, the space-time yield decreases. In the present invention, the residual gas obtained after the nitrile compound of the object compound is separated from the reaction gas discharged from the reactor is recycled to the reactor of ammoxidation. When oxygen is contained in the residual gas in an amount more than the negligible amount, the amount of fresh supply of the air may be suitably adjusted since the above ratio $O_2$/organic substituent must be controlled.

The pressure of ammoxidation may be any of the atmospheric pressure, an added pressure and a reduced pressure. It is preferable that the pressure is in the range of around the atmospheric pressure to 0.2 MPa. The contact time between the reaction gas and the catalyst is varied depending on the conditions such as the type of the compound having organic substituents, the composition of the supplied raw materials and the temperature of the reaction. The contact time is, in general, in the range of 0.5 to 30 seconds.

The temperature of the reaction is in the range of 300 to 500° C. and preferably in the range of 330 to 470° C. When the temperature is lower than the above range, a sufficient rate of reaction is not obtained. When the temperature exceeds the above range, the amount of byproducts such as carbon dioxide and hydrogen cyanide increases and the yield of the nitrile compound decreases. The temperature of the reaction is suitably decided so as to provide the optimum yield under the above conditions with consideration on the change in the activity of the catalyst.

In the present invention, the residual gas component, which is obtained after the nitrile compound of the object compound is separated from the reaction gas discharged at the outlet of the reactor, is recycled to the reactor. Examples of the process for separating and recovering the nitrile compound from the reaction gas include the following processes (1) and (2). (1) A process in which the reaction gas is brought into contact with an organic solvent dissolving the nitrile compound so that the nitrile compound is collected with the solvent and separated from the residual gas components. (2) A process in which the reaction gas is cooled so that the nitrile compound is separated or condensed as a solid or a liquid and separated from the residual gas components. In process (1), an organic solvent such as an alkylbenzene, a heterocyclic compound, a carbon ring nitrile and a heterocyclic nitrile is used as the above solvent. It is preferable that a nitrile compound formed in the ammoxidation such as a mononitrile compound is used since the number of the substances in the process does not increase. For example, it is preferable that meta-tolunitrile formed as the byproduct in the ammoxidation is used when isophthalonitrile is obtained from meta-xylene.

The residual gas obtained after the separation of the nitrile compound comprises molecular nitrogen gas as the main component, molecular oxygen gas, ammonia, carbon dioxide, carbon monoxide, hydrogen cyanide, water and the unreacted compound having organic substituents. The residual gas may be supplied to the reactor of ammoxidation without any treatments. Where necessary, components such as water, carbon dioxide, hydrogen cyanide, ammonia and the unreacted compound having organic substituents are removed from the residual gas and the resultant gas containing molecular nitrogen gas as the main component may be recycled to the reactor of ammoxidation. The present inventors proposed in Japanese Patent Application Laid-Open No. 2001-348370 a process in which unreacted ammonia and hydrogen cyanide are separated and recovered by absorption with water from a residual gas obtained by separating a nitrile compound and these compounds are recycled to the reaction system. The residual gas from which the nitrile compound, ammonia and hydrogen cyanide have been separated may be obtained from the reaction gas discharged at the outlet of the reactor, for example, in accordance with this process and recycled to the reactor of ammoxidation.

The residual gas after the separation of the nitrile compound contains molecular nitrogen gas in an amount of more than 50% by volume. The residual gas after the separation of the nitrile compound, ammonia and hydrogen cyanide by absorption with water contains molecular nitrogen gas in an amount of more than 80% by volume.

In the present invention, the amount of the residual gas recycled to the reactor is in the range of 10 to 60% by volume and preferably in the range of 15 to 50% by volume based on the amount of the fresh raw material gas comprising the compound having organic substituents, ammonia and the air which are freshly supplied to the reactor. When the amount of the recycled residual gas is less than the above range, the effect of the present invention is not sufficiently obtained. When the amount of the recycled residual gas exceeds the above range, the amount of the recycled substances increases and the space-time yield decreases. In the present invention, % by volume means the percentage of the volumes at the so-called standard state, i.e., at 0° C. under the atmospheric pressure. In the process of the present invention in which the residual gas is recycled to the reactor of ammoxidation, the reaction is conducted while the ratio of the amount by mole of molecular oxygen to the number of the organic substituent in the compound having organic substituents supplied to the reactor ($O_2$/organic substituent) is kept in a range of 1.5 to 7 and preferably in the range of 1.5 to 5. Therefore, in the present invention, the amount of the recycled residual gas and the amount of the supplied air are adjusted in a manner such that the ratio of the amount by volume of the recycled residual gas to the amount by volume of the gas of the fresh raw material (the amount of recycled residual gas/the amount of gas of the fresh raw material) is in the range of 10 to 60% and $O_2$/organic substituent is in the range of 1.5 to 7. For adjusting the amount of the supplied substances, the concentration of molecular oxygen gas in the recycled residual gas is measured and the suitable amounts of the supplied substances can be decided based on the result. The concentration of molecular oxygen gas in the recycled residual gas can be easily measured in accordance with the gas chromatography or by using a commercial sensor of the oxygen concentration. The effect of increasing the yield can be obtained by supplying the optimum amount of the residual gas containing molecular nitrogen gas as the main component while the relative amounts expressed by $O_2$/organic substituent is controlled within the suitable range.

In the present invention, the concentration of the compound having organic substituents in the gas supplied to the reactor is in the range of 0.2 to 10% by volume and preferably in the range of 0.5 to 5% by volume. When the concentration exceeds the above range, the yield of the nitrile compound decreases. When the concentration is smaller than the above range, the space-time yield decreases. When the process of the present invention is conducted, the excellent yield can be obtained by adjusting the concentration of the compound having organic substituents to 0.07 moles or smaller as expressed by the amount by mole of the organic substituent per 1 mole of the entire components supplied to the reactor. In this condition, the effect of the present invention is more effectively exhibited. The amount by mole of the organic substituent per 1 mole of the entire components supplied to the reactor means the value obtained by multiplying the concentration by volume of the compound having organic substituents by the number of the organic substituent in the compound having organic substituents. For example, xylene having two methyl groups as the organic substituents in an amount of 1.5% by volume gives a concentration of the organic substituent of 0.015× 2=0.03 moles per 1 mole of the entire components supplied to the reactor.

FIG. 1 shows a flow diagram exhibiting an embodiment of the process of the present invention. In this embodiment, the ammoxidation is conducted in accordance with the reaction using a fluidized bed. The reaction gas discharged from the reactor is brought into contact with a solvent and the reaction products are collected. The residual gas obtained after this step is brought into contact with water and ammonia is collected. The residual gas obtained after these steps is recycled to the reactor of ammoxidation. In FIG. 1, 1 means a reactor of ammoxidation, 2 means a column for collecting a nitrile and 3 means a column for washing with water.

In FIG. 1, a reactor of ammoxidation 1 is packed with the fluidized catalyst. To the reactor, the compound having organic substituents, ammonia, the air and the recycled residual gas are supplied and the ammoxidation is conducted. A cooling tube is disposed at the inside of the reactor and the surface of the fluidized catalyst bed is placed at a lower portion of the upper end portion of the cooling tube. After particles of the catalyst in the reaction gas are separated by a catalyst cyclone and returned to the fluidized catalyst bed via a tube for returning the catalyst, the reaction gas is discharged via a tube for discharge. The reaction gas discharged from the reactor contains the nitrile compound, ammonia, hydrogen cyanide, carbon dioxide, water, carbon monoxide, molecular nitrogen gas, molecular oxygen gas and the unreacted compound having organic substituents. The reaction gas is transferred to a column for collecting a nitrile 2 of the next step. In the column for collecting a nitrile 2, the reaction gas and the solvent are brought into contact with each other and the nitrile compound contained in the reaction gas is collected. The residual gas obtained after the nitrile compound is collected is transferred to a column for washing with water 3. In the column for washing with water, the residual gas and water are brought into contact with each other and ammonia and hydrogen cyanide contained in the reaction gas are collected. A portion of the residual gas obtained from the column for washing with water is recycled to the reactor of ammoxidation and the remaining amount of the residual gas is introduced into an apparatus for treating a gas for disposal such as an incinerator.

EXAMPLES

The present invention will be described more specifically with reference to Example and Comparative Example in the following. However, the present invention is not limited to Example and Comparative Example.

In the following Example and Comparative Example, the results of the reaction are based on the amount of supply of meta-xylene (MX).

<Preparation of a Catalyst>

To 229 g of vanadium pentoxide $V_2O_5$, 500 ml of water was added. The resultant mixture was heated at 80 to 90° C.

and 477 g of oxalic acid was added under sufficient stirring and dissolved. Separately, 400 ml of water was added to 963 g of oxalic acid and the resultant mixture was heated at 50 to 60° C. To the obtained solution, a solution obtained by adding 252 g of chromic acid anhydride $CrO_3$ into 200 ml of water was added under sufficient stirring and dissolved. To the solution of vanadium oxalate obtained above, the solution of chromium oxalate obtained above was mixed at 50 to 60° C. and a vanadium-chromium solution was obtained. To the obtained solution, a solution obtained by dissolving 41.1 g of phosphomolybdic acid $H_3(PMo_{12}O_{40}).20H_2O$ into 100 ml of water Was added. To the resultant solution, a solution obtained by dissolving 4.0 g of potassium acetate $CH_3COOK$ into 100 ml of water was added and, then, 2,500 g of a 20% by weight aqueous silica sol (containing 0.02% by weight of $Na_2O$) was added. To the obtained slurry, 78 g of boric acid $H_3BO_3$ was added and sufficiently mixed. The resultant fluid was concentrated by heating until the amount of the fluid became about 3,800 g. The obtained catalyst solution was dried by spraying while the temperature at the inlet was kept at 250° C. and the temperature at the outlet was kept at 130° C. The catalyst obtained after the drying by spraying was dried in a drier at 130° C. for 12 hours and calcined at 400° C. for 0.5 hours and, then, at 550° C. for 8 hours under a stream of the air and a fluidized catalyst was prepared. The catalyst contained the components in amounts such that the ratio by atom of the components V:Cr:B:Mo: P:Na:K was 1:1:0.5:0.086:0.007:0.009:0.020 and the concentration of the catalyst components in the fluidized catalyst was 50% by weight.

Comparative Example 1

The ammoxidation of meta-xylene was conducted using the reactor of ammoxidation shown in FIG. 1. The reactor of ammoxidation was packed with 2,300 kg of the fluidized catalyst prepared above. The air, meta-xylene (MX) and ammonia gas were preheated at 180° C. and supplied to the reactor. The amount of supply of MX was 242 kg/hr, the amount of supply of ammonia was 342 kg/hr and the amount of supply of the air was 1,390 $Nm^3$/hr. The reaction was conducted under a pressure of the reaction of 0.08 MPa and isophthalonitrile (IPN) was obtained. The reaction gas was introduced into a column for collecting a nitrile and the nitrile compound contained in the reaction gas was collected. The residual gas obtained after the collection of the nitrile compound was introduced into a column for washing with water and brought into contact with water and ammonia and hydrogen cyanide contained in the reaction gas was collected. The entire amount of the residual gas discharged from the column for washing with water was introduced into an apparatus for treating the gas for disposal without recycling to the reactor of ammoxidation.

When the temperature of the reaction was adjusted, the yield of IPN showed the maximum value at a temperature of the reaction of 431° C. The results of the reaction were as follows: the yield of IPN: 82.3% by mole; the yield of meta-tolunitrile: 1.3%; and the yield of components formed by burning (carbon dioxide, carbon monoxide and hydrogen cyanide): 13.5%.

Example 1

The reaction was conducted in accordance with the same procedures as those conducted in Comparative Example 1 except that the residual gas discharged from the column for washing with water in an amount of 830 $Nm^3$/h was recycled to the reactor of ammoxidation, the amount of supply of the air was 1,200 $Nm^3$/h and the temperature of the reaction was 441° C. The concentration of oxygen in the residual gas obtained from the column for washing with water 3 was 5.2% by volume. The amount of the recycled residual gas was 48.8% by mole based on the amount of fresh supply of the raw material gas, $O_2$/organic substituent was 2.9 and the ratio of the amount by mole of the organic substituent to the amount by mole of the entire components supplied to the reactor was 0.040.

The results of the reaction were as follows: the yield of IPN: 87.1% by mole; the yield of meta-tolunitrile: 4.1%; and the yield of components formed by burning (carbon dioxide, carbon monoxide and hydrogen cyanide): 6.2%. The yield of IPN increased from that in Comparative Example 1.

Example 2

The reaction was conducted in accordance with the same procedures as those conducted in Comparative Example 1 except that the residual gas discharged from the column for washing with water in an amount of 650 $Nm^3$/h was recycled to the reactor of ammoxidation, the amount of supply of the air was 1,300 $Nm^3$/h and the temperature of the reaction was 438° C. The concentration of oxygen in the residual gas obtained from the column for washing with water 3 was 5.6% by volume. The amount of the recycled residual gas was 36.1% by mole based on the amount of fresh supply of the raw material gas, $O_2$/organic substituent was 3.0 and the ratio of the amount by mole of the organic substituent to the amount by mole of the entire components supplied to the reactor was 0.042.

The results of the reaction were as follows: the yield of IPN: 86.1% by mole; the yield of meta-tolunitrile: 3.3%; and the yield of components formed by burning (carbon dioxide, carbon monoxide and hydrogen cyanide): 8.4%. The yield of IPN increased from that in Comparative Example 1.

Example 3

The reaction was conducted in accordance with the same procedures as those conducted in Comparative Example 1 except that the residual gas discharged from the column for washing with water in an amount of 350 $Nm^3$/h was recycled to the reactor of ammoxidation, the amount of supply of the air was 1,320 $Nm^3$/h and the temperature of the reaction was 433° C. The concentration of oxygen in the residual gas obtained from the column for washing with water 3 was 4.6% by volume. The amount of the recycled residual gas was 19.2% by mole based on the amount of fresh supply of the raw material gas, $O_2$/organic substituent was 2.9 and the ratio of the amount by mole of the organic substituent to the amount by mole of the entire components supplied to the reactor was 0.047.

The results of the reaction were as follows: the yield of IPN: 84.2% by mole; the yield of meta-tolunitrile: 1.9%; and the yield of components formed by burning (carbon dioxide, carbon monoxide and hydrogen cyanide): 12.1%. The yield of IPN increased from that in Comparative Example 1.

What is claimed is:

1. A process for producing a nitrile compound which comprises introducing meta-xylene into a reactor in combination with ammonia and an air and ammoxidizing the introduced compound in the gas phase, in a presence of a catalyst including an oxide of at least one element selected from the group consisting of vanadium, molybdenum and iron, wherein, during the reaction, a residual gas component comprising nitrogen gas as a main component, containing molecular nitrogen in an amount of more than 50% by volume, which is obtained after the formed nitrile compound is separated from a reaction gas discharged from the reactor, is recycled to the reactor in an amount in a range of 10 to 60% by volume based on an amount of a fresh raw material gas comprising meta-xylene, ammonia and the air which are freshly supplied to the reactor, and a ratio of an amount by mole of molecular oxygen to an amount by mole of the organic substituents in the meta-xylene supplied to the reactor ($O_2$/organic substituent) is kept in a range of 1.5 to 7.

2. A process according to claim 1, wherein an amount of the organic substituents in the meta-xylene supplied to the reactor is 0.07 moles or less per 1 mole of entire components supplied to the reactor.

3. A process according to claim 1, wherein the nitrile compound is collected by bringing the reaction gas discharged from the reactor into contact with a solvent.

4. A process according to claim 1, wherein the ammoxidation is conducted in a fluidized bed reactor.

5. A process according to claim 1, wherein the nitrile compound is isophthalonitrile.

6. A process according to claim 1, wherein the ammoxidizing is performed in a fixed bed reactor, a moving bed reactor or a fluidized bed reactor.

7. A process according to claim 1, wherein the amount of ammonia introduced into the reactor, expressed as a ratio of amount of moles of ammonia to the amount of moles of the organic substituent in the meta-xylene, is in a range of 1 to 10.

8. A process according to claim 7, wherein the amount of ammonia introduced into the reactor, expressed as said ratio of amount of moles of ammonia to the amount of the moles of the organic substituent, is in the range of 3 to 7.

9. A process according to claim 8, wherein said ratio of an amount by mole of molecular oxygen to the amount by mole of the organic substituent is kept in a range of 1.5 to 5.

10. A process according to claim 1, wherein said residual gas component is recycled to the reactor in an amount in the range of 15 to 50% by volume based on the amount of said fresh raw material gas freshly supplied to the reactor.

11. A process according to claim 1, wherein a concentration of meta-xylene introduced into the reactor is 0.2 to 10% by volume.

12. A process according to claim 1, wherein the residual gas component comprising nitrogen gas as a main component is recovered after absorption with water from a residual gas obtained from the reaction gas discharged from the reactor, after separation of the nitrile compound from the reaction gas.

13. A process according to claim 12, wherein the residual gas component comprising nitrogen gas as a main component after absorption with water contains molecular nitrogen gas in an amount of more than 80% by volume.

14. A process for producing a nitrile compound which comprises introducing at least one carbon ring compound having organic substituents or heterocyclic compound having organic substituents, that can be ammoxidized in the presence of an ammoxidation catalyst for an ammoxidation reaction to form said nitrile compound, into a reactor in combination with ammonia and an air and ammoxidizing the introduced compound, in the gas phase, in the presence of the catalyst for the ammoxidation reaction, wherein, during the reaction, a residual gas component comprising nitrogen gas as a main component, containing molecular nitrogen in an amount of more than 50% by volume, which is obtained after the formed nitrile compound is separated from a reaction gas discharged from the reactor, is recycled to the reactor in an amount in a range of 10 to 60% by volume based on an amount of a fresh raw material gas comprising the carbon ring compound having organic substituents or the heterocyclic compound having organic substituents, ammonia and the air which are freshly supplied to the reactor, and a ratio of an amount by mole of molecular oxygen to an amount by mole of the organic substituent in the carbon ring compound having organic substituents or the heterocyclic compound having organic substituents supplied to the reactor ($O_2$/organic substituent) is kept in a range of 1.5 to 7, wherein the carbon ring compound has a carbon ring selected from the group consisting of a benzene ring, a naphthalene ring, an anthracene ring, a cyclohexane ring, a cyclohexene ring, a dihydronaphthalene ring, a tetraline ring and a decaline ring, and the heterocyclic compound has a heterocyclic ring selected from the group consisting of furan ring, pyrrol ring, indole ring, thiophene ring, pyrazole ring, imidazole ring, oxazole ring, pyran ring, pyridine ring, quinoline ring, isoquinoline ring, pyrroline ring, pyrrolidine ring, imidazoline ring, imidazolidine ring, piperidine ring and piperadine ring.

15. A process according to claim 14, wherein said ammoxidation catalyst includes an oxide of at least one element selected from the group consisting of vanadium, molybdenum and iron.

16. A process according to claim 14, wherein the organic substituents of the carbon ring compound and of the heterocyclic compound are selected from the group consisting of methyl, ethyl, propyl, formyl, acetyl, hydroxymethyl and methoxycarbonyl.

* * * * *